United States Patent [19]

White et al.

[11] 4,043,941

[45] Aug. 23, 1977

[54] SUPPORTED TRANSITION METAL CATALYSTS AND PROCESS FOR THEIR PREPARATION

[75] Inventors: John F. White; Jerome C. Bertrand, both of Cincinnati, Ohio

[73] Assignee: Emery Industries, Inc., Cincinnati, Ohio

[21] Appl. No.: 635,467

[22] Filed: Nov. 26, 1975

[51] Int. Cl.$^2$ .............................................. B01J 31/02
[52] U.S. Cl. ..................................... 252/430; 252/428
[58] Field of Search ............................... 252/428, 430

[56] References Cited

U.S. PATENT DOCUMENTS

| 3,677,970 | 7/1972 | Mertzweiller | 252/430 X |
| 3,773,742 | 4/1973 | Kruce | 252/428 X |
| 3,817,931 | 6/1974 | Brooks et al. | 252/428 X |
| 3,840,511 | 10/1974 | Ballard et al. | 252/428 X |

Primary Examiner—Patrick P. Garvin
Assistant Examiner—Niebling, John F.
Attorney, Agent, or Firm—Gerald A. Baracka; John D. Rice

[57] ABSTRACT

An improved process is provided herein for the preparation of immobilized transition metal catalysts containing up to about 60 wt. % bound transition metal. These catalysts are obtained by heating a hydroxylic support with an excess of a transition metal alkoxide in an inert hydrocarbon and in the presence of water.

28 Claims, No Drawings

SUPPORTED TRANSITION METAL CATALYSTS AND PROCESS FOR THEIR PREPARATION

BACKGROUND OF THE INVENTION

Numerous heavy metals, especially transition metals, have been bonded to the surface of various support materials by reaction of a metal compound with the surface hydroxyl groups. In this way it has been possible to obtain supported catalysts useful for widely diverse applications such as polymerization esterification, hydrogenation oxidation, hydroformylation and the like.

Probably the most common method of bonding a metal to a support is by the reaction of the surface hydroxyl with a metal halide compound. For example, U.S. Pat. No. 3,166,543 shows the reaction of carbon blacks, such as channel carbon blacks which have hydroxyl groups on their surface, with a transition metal halide, e.g. titanium tetrachloride, and subsequently heating with a silane compound to obtain a useful olefin polymerization catalyst. U.S. Pat. No. 3,166,542 similarly discloses polymerization catalysts obtained in much the same manner but where the support material is a finely divided inorganic solid such as alumina, titania, zirconia, thoria, magnesia, silicates or aluminates.

Other methods of attachment are also known. For example, hydroformylation catalysts containing units of the formula

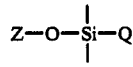

where Z represents the support and Q is a group containing phosphorus bonded to a transition metal are described in U.S. Pat. No. 3,832,404 and obtained by (i) reacting a transition metal compound with a compound containing silicon and phosphorus e.g. (EtO)$_3$Si(CH$_2$)$_2$PR$_2$ to form a compound containing transition metal bonded to phosphorus and reacting this latter compound with an inorganic solid containing — OH groups or (ii) reacting the inorganic solid with the compound containing silicon and phosphorus and then reacting this product wth the transition metal compound. Transition metal amine compounds, such as tetrakisdiethylaminotitanium, tetrakisdimethylaminozirconium and dichlorodibutylaminotitanium, have also been shown in U.S. Pat. No. 3,392,160 to react with hydroxyl-containing finely divided particulate supports and are then activated by further reaction with an organometallic compound. U.S. Pat. No. 3,816,340 shows the preparation of olefin disproportionation catalysts by reacting a substantially inert matrix having a hydroxylic surface with a transition metal complex such as tetrakis ($\pi$-allyl) tungsten or molybdenum.

It is also known to react various metal compounds containing one or more alkoxide groups with hydroxy-bearing support materials. U.S. Pat. No. 3,326,877 discloses polymerization catalysts obtained by reacting a finely divided inorganic support with compounds of the formula T(Q)$_n$ where T is a Group IVa, Va or VIa metal and Q is an alkoxy or aryloxy radical and then further reacting with an organometallic compound. This process requires that the support and any diluents or carrier gases be essentially anhydrous when the transition metal ester is contactedwith the support. The presence of water prevents the desired chemical reaction and produces an inferior catalyst component or subsequent reaction with the organometallic compound. No more than transition metal atom is present per surface hydroxyl group and very low levels of transition metal are bound to the support. Similarly, U.S. Pat. No. 3,817,931 discloses catalysts suitable for the production of polyesters which are obtained by reacting a hydroxy-bearing support with metal compounds, including germanium, titanium, zirconium and hafnium alkoxides, in addition to metal halides and organometallic compound. Each metal atom is linked to the support by from 1 to $n-1$ (where $n$ is the valence of the metal) oxygen linkages (—O—) and the concentration of the bound metal is very low.

Still another reference, U.S. Pat. No. 3,622,522, discloses olefin polymerization catalysts containing up to 15 wt. % gallium and/or tin with up to 50 wt. % chromium. These catalysts are obtained by depositing a chromium compound, such as chromium trioxide, and at least one compound selected from the group of gallium and tin alkoxides or aryloxides with a support and then heating at a temperature of at least 1700° F. The metal compounds preferably are deposited on the support from a nonaqueous solvent or dispersant and the heating is carried out in substantially water free (less than 0.1 wt. % water) air or a stream of oxygen-containing gas.

It would be extremely advantageous if highly active supported transition metal catalysts could be prepared from transition metal alkoxides without taking precautions to exclude moisture normally present on the hydroxylic support material or otherwise present in the reaction system from solvents, diluents, air or carrier gases. It would be even more advantageous if the process could be conducted as a single-step reaction and without subsequent calcining at temperatures of 350° C or higher. The process and catalyst would be even more desirable if it were possible to vary the amount of transition metal bound to the support from small amounts up to very high levels. It would be even more advantageous if the catalysts were recoverable directly from the reaction as free-flowing powders by simply filtering, washing and air-drying and if such products exhibited good catalytic activity.

SUMMARY OF THE INVENTION

We have now discovered an improved process and catalysts wherein all the aforementioned advantages are realized. Furthermore, we have quite unexpectedly discovered that in our process the presence of water is essential to the conduct of the reaction rather than being a detriment as would be expected from the teachings of the prior art. The supported catalysts obtained from this process have high activity and good stability in the presence of water and are free-flowing powders. They have greater than monomeric attachment of the transition metal compound, i.e., more than one transition metal atom bound per available surface hydroxyl group, and the catalysts can contain up to 60% or more bound transition metal. The present transition metal catalysts are extremely useful in esterification processes.

The present improved process involves heating a hydroxylic support with a molar excess (based on the available hydroxyl groups) of the transition metal alkoxide at a temperature in the range 100°–300° C with agitation in an aliphatic hydrocarbon and in the presence of water. In addition to reaction with the surface hydroxyl groups, self-condensation of the transition metal alkoxide also occurs so that a cross-linked matrix of transition metal atoms having bridging oxygen linkages (—O—) covers and is bonded to the support. Useful transition metal alkoxides have the formula $$M(OR)_nQ_m$$

where M is a transition metal selected from Groups IVb, Vb and VIb, OR is an alkoxy radical containing 1 to 18 carbon atoms, n is an integer from 2 up to the valence of the metal M, Q is an inert group which will not react with the hydroxyl groups of the support, the alkoxide radical OR or alcohol ROH formed therefrom and m is an integer so that $n + m$ satisfies the valence of the metal M. Supports can be any of the commonly available support materials containing a plurality of hydroxyl groups on the surface thereof.

The process will generally be conducted at a temperature from 120°–250° C in a saturated aliphatic hydrocarbon such as the mineral oils. Transition metal alkoxides where in the — OR radical is a saturated branched or straightchain alkoxy radical containing 2 to 8 carbon atoms and the metal is titanium, zirconium, hafnium or vanadium are most useful and titanium tetraalkoxides are especially preferred. The water may be present at the outset of the reaction, either added as such or adsorbed on the support, may be added subsequently, or formed in situ by dehydrating alcohol by-products. An excess of the transition metal alkoxide is required in order that greater than monomeric attachment, i.e. more than one Ti atom bonded per available surface hydroxyl, will be obtained. The ratio of transition metal alkoxide molecules reacted per hydroxyl group will therefore be greater than 1:1 and can range as high as $10^6:1$.

The catalysts are free-flowing powders containing from about 3 wt. % up to about 60 wt. % or higher transition metal bound to the support. The immobilized catalysts are the result of a highly cross-linked matrix of transiton metal atoms having bridging oxygen linages (—O—) covering and bonded to the support. This rigid metal oxide polymerix array having multiple attachments of the polymer to the support will still contain sufficient alkoxide groups to be catalytically active.

DETAILED DESCRIPTION

The present improved process deals with the preparation of supported transition metal catalysts by the reaction of a hydroxylic support material and a transition metal alkoxide. Useful transition metal compounds for this process have the general formula $$M(OR)_nQ_m$$

where M is a transition metal selected from Groups IVb, Vb and VIb, OR is an alkoxy radical containing 1 to 18 carbon atoms, such as ethoxy, n-propoxy isopropoxy, n-butoxy, isobutoxy, tert-butoxy, n-octoxy, 2-ethylhexyloxy, n-decyloxy, allyloxy, tridecyloxy stearyloxy, isotridecyloxy, cyclopentyloxy, cyclohexyloxy, and the like, n is an integer from 2 up to the valence o the metal M, Q is an inert group which will not react with the hydroxyl groups of the support, an alkoxide radical OR or alcohol ROH formed therefrom, and m is an integer so that $n + m$ satisfies the valence of the transition metal M. The metal groups referred to herein are from the Periodic Table set forth on the inside cover of the Handbook of Chemistry and Physics, 56the edition, 1975-76, CRC Press Cleveland, Ohio. Especially useful transition metal compounds are those wherein the —OR radical is a saturated branched or straight-chain alkoxy radical containing 2 to 8 carbon atoms and the transition metal is titanium, zirconium, hafnium or vanadium. Illustrative transition metal compounds include but are not limited to tetraethoxy titanium, tetraisopropoxy titanium, tertrabutoxy titanium, tetraisobutoxy titanium, dimethoxydibutoxy titanium, methoxybutoxydiisospropoxy titanium, methoxyisopropoxydibutoxy titanium, tetrabutoxy vanadium, tetrabutoxy zirconium, tetraisopropoxy zirconium, pentamethoxy vanadium, pentaisopropoxy vanadium, triisopropyl vanadate, tributyl vanadate, tetraisopropoxy hafnium, chromium(II) isopropoxide, chromium(II) dodecyloxide, chromium(IV) isopropoxide, chromium(VI) ethoxide and the like. Transition metal compounds containing a metalloketone group

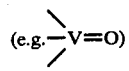

(e.g. $-V=O$)

can also be used for the process of this invention as can other compounds containing inert groups, i.e. which do not interfere with the reaction. Especially useful transition metal compounds for this invention have all their available valences satisfied with a saturated alkoxide radical and titanium tetraalkoxides are an especially preferred embodiment.

In the present process, the above-described transition metal compounds are reacted with any of the conventional and commonly used support materials having a hydroxylic surface, that is, containing a plurality of hydroxyl groups attached to the surface of the matrix. The surface hydroxyl groups provide the sites of attachment of the transition metal to the support which can be represented

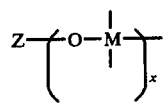

where Z represents the support matrix and M is a tetravalent transition metal with x indicating the number of such attachments (corresponding to the number of available hydroxyl groups) present on the support. Suports may be either synthetically produced or naturally occuring materials and can be anhydrous or contain moisture. Particle size may also vary widely, in fact, the process is also useful where the support material is in the shape of spheres, hollow tubes, rings, rods, fibers, platelets or like forms. It will be noted, however, that the present improved process has particular application to finely divided supports and the larger the surface area and the higher the number of surface hydroxyl groups, the greater the potential reactivity of the support with the transition metal compound.

To illustrate the large number and widely diverse types of supports which can be used in this process, it should be pointed out that even carbon blacks having hydroxyl groups on their surface, such as channel carbon blacks and furnace carbon blacks, can be effectively utilized. Similarly, synthetic inorganic oxides of silicon, magnesium, aluminum, zinc and mixtures thereof are also useful supports. Organic polymers having pendant hydroxyl functionality or functionality which can be converted to hydroxyl groups can be used. Matrix materials of silica and alumina or mixtures thereof, which can also contain small amounts of alkali and alkaline earth oxides, iron oxide, zinc oxide and the like, are especially useful because of their ready availability from natural sources. These supports may be used as such or they may be further activated such as by acid treatment or the like.

A partial and non-limiting list of suitable inorganic solid supports includes alumina, silica, fumed silica, silica gel, naturally occurring clays such as the kaolinite type, the smectite type particularly montmorillonite clay, the vermiculite type, the palygorskite type, the chlorite and mica type and the like, zeolites, zirconia, titania, thoria, magnesia, aluminates such as bauxite and corundum, silicates such as chrysotile, actinolite and the like.

Because of the ability of the process to form a highly cross-linked transition metal-containing polymeric coating over the surface of the support by the condensation of the transition metal alkoxide, it is not necessary that the support contain a high concentration of hydroxyl groups to obtain an active catalyst having a high weight percent bound transition metal. This is contrary to the teachings of the prior art where the transition metal content was directly proportional to the amount of reacted surface hydroxyl. It is theoretically possible employing the present improved process to have a catalyst support wherein the transition metal polymer totally coats the support and is immobilized yet bonded to a support matrix by only one —OH group. It will be evident, however, that a greater number of surface hydroxyl groups facilitate the reaction and enables one to completely coat the support more uniformly and with greater efficiency. For this reason it is preferred that the support contain a plurality of hydroxyl groups. There is of course no upper limit to the amount of hydroxyl groups present on the support matrix.

By the improved process of this invention it is possible to obtain supported catalysts having superior activity and containing significantly higher amounts of the transition metal bound to the support, i.e. immobilized, so that the transition metal will not be lost from the catalyst during the subsequent reaction where it is employed. For esterification reactions, in addition to the increased catalytic activity these catalysts give improvement in color and stability of the ester products obtained and make it possible to obtain ester products having very low residual transition metal contents. The improvement of this invention consists of heating the hydroxylic support with an excess of the transition metal alkoxide in an inert hydrocarbon medium in the presence of water at an elevated temperature and with agitation to effect condensation of the transition metal alkoxide and reaction with the surface hydroxyl groups.

It is believed, although there is no intent to be bound by the following explanation and equations, that the reaction between the support and the transition metal alkoxide can be represented as follows:

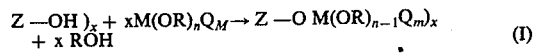

where Z, M, R, Q, $x$, $n$ and $m$ are as defined above. The above equation also describes what has been taught by the prior art where the reactions have been conducted under anhydrous or essentially anhydrous conditions. In the present invention, however, where the process is conducted in a suitable reaction medium, in the presence of water and with an excess of the transition metal alkoxide (based on the available surface —OH groups), polycondensation of the transition metal alkoxide occurs resulting in a cross-linked transition metal oxide polymer which is bound to the surface of the support. From the above equation it is evident that by an excess of the transition metal alkoxide is meant a molar amount greater than $x$ or more than one molecule transition metal alkoxide reacted per available surface hydroxyl group. While it is theoretically possible for all of the surface —OH groups to be reacted in the above manner it is not necessary. Since the transition metal alkoxide undergoes polymerization (self-condensation) it is still possible for all the transition metal charged to be incorporated on the support and obtain high levels of transition metal bound thereto with the result that extremely active and useful catalysts are obtained.

In the case where the transition metal alkoxide is a titanium alkoxide of the formula $Ti(OR)_4$ and considering the reaction at a single hydroxyl group the reaction will be represented by the equation:

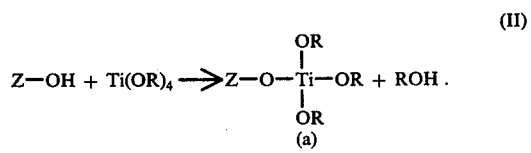

However, when additional transition metal compound is available and in the presence of water to drive the reaction, condensation can occur at any or all of the OR groups of the moiety (a). Considering the reaction at only one of the OR groups the reaction would be represented as follows:

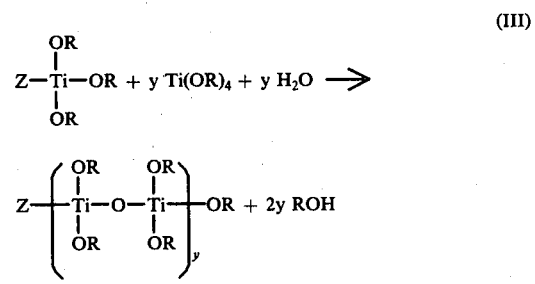

It will be evident that any of the other —OR groups can also undergo reaction in the same manner and also that condensation with adjacent —OR moieties from different pendant groups can occur with the result that a highly complex cross-linked titanate polymer is obtained on the surface of the substrate. Those skilled in the art will also recognize that it is also possible for some condensation (polymerization) to occur prior to reaction with a surface hydroxyl group as shown in equation II. The extent of condensation will be primarily dependent on the amount of transition metal alkoxide, the availability of water to drive the reaction and the reaction conditions whereas the amount of cross-linking is also a function of the particular transition metal alkoxide used, i.e. the number of alkoxide substituents available for reaction. The above equations are merely intended to be illustrative and represent the overall reaction without taking into account the stepwise manner by which a particular reaction may occur.

To obtain the improved supported catalysts of this invention the process is conducted at an elevated temperature from about 100° C to about 300° C. The temperature is governed by the particular transition metal alkoxide employed, the amount of water present in the reaction mixture at the outset of the reaction and the rate and extent of reaction desired. It will be evident that while it may be possible to carry out the process at 100° C the rate may be such as to make the process impractical and thus it would be advantageous to increase the reaction temperature since the resulting products will be essentially the same. It is generally most advantageous to conduct the reaction at a temperature in the range 120° to 250° C. The reaction can be conducted at atmospheric pressure or in a closed vessel at pressures up to about 1000 psig and, more preferably, up to about 500 psig. To some extent the temperature will govern whether the reaction is conducted in an open or closed vessel. When conducting the process at atmospheric pressure, it may be carried out under an inert atmosphere of nitrogen, argon or the like, however, this is not necessary. A carrier gas may be employed to facilitate removal of alcohol and other by-products formed during the reaction. While numerous variations are possible, excellent results are obtained when the reaction is conducted at atmospheric pressure in the presence of air while venting any by-product gases and condensing and collecting in a suitable trap the alcohol forming during condensation.

To obtain the improved immobilized transition metal catalyst it is necessary that a suitable hydrocarbon be employed as the reaction medium. While the exact role of the hydrocarbon is not precisely known, in addition to the normal function of such reaction media to evenly distribute the heat and thus provide for a more controllable rate of reaction, it is theorized that it also serves to solubilize the transition metal alkoxide and coat the surface of the support to prevent agglomeration of the finely divided catalyst particles. The hydrocarbon also facilitates recovery of the final immobilized catalyst product. Useful aliphatic hydrocarbons include the normal paraffins ($C_nH_{2n+2}$), isoparaffins ($C_nH_{2n+2}$), olefins ($C_nH_{2n}$), diolefins ($C_nH_{2n-2}$) and cycloparaffins ($C_nH_{2n}$) and mixtures thereof. Aromatic hydrocarbons may also be present in the mixture. It is generally desirable to use hydrocarbons which are predominantly saturated since the presence of excessive amounts of olefinic unsaturation results in undesirable color formation, particularly if the process is conducted in the presence of air. When the hydrocarbon is predominantly an aliphatic saturated hydrocarbon such problems are avoided. The aliphatic hydrocarbon reaction medium can consist of normal paraffins, isoparaffins, cycloparaffins or mixtures thereof with small amounts of olefins. These hydrocarbons can contain from about 8 to about 40 carbon atoms and are usually obtained by the fractional distillation of paraffin-base petroleum fractions. They generally consist of mixtures of oily liquid hydrocarbons in the range of $C_{14-32}$. For the purpose of this invention it is especially useful that the aliphatic hydrocarbon be a liquid at about 30° C or below and have a boiling point greater than about 140° C. Useful aliphatic hydrocarbons include but are not limited to liquid petrolatum, liquid paraffin and the numerous commercially available mineral oils and mineral seal oils. In general, the ratio of hydrocarbon oil to support will range from about 0.5:1 to about 50:1 and, more preferably, between about 2:1 and 25:1, on a weight basis.

As already indicated the presence of water is essential in order to obtain the highly active immobilized catalysts of this invention. While the surface hydroxyl group can react with the titanium alkoxide without water, subsequent reaction (condensation) will not occur if anhydrous conditions are maintained. Since one mole of water is required for each bridging oxygen linkage formed (see equation III) at least one mole water per mole transition metal alkoxide to be condensed is required for polycondensation. The presence of larger amounts of water (even as high as a ten-fold mole excess) does not, however, detract from the reaction or activity of the resulting catalyst. For this invention water may be added at the outset of the reaction, charged continuously or intermittently during the course of the reaction, or formed in situ. Any of these procedures may also be combined to achieve the required amount of water necessary to drive the condensation reaction. In the case of a titanium alkoxide the overall reaction can be represented as follows:

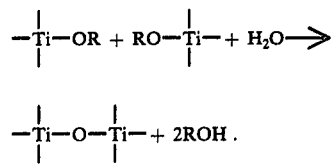

(IV)

It is not necessary, however, that all the required water, based on the transition metal alkoxide charged, be present at the outset of the reaction. It will suffice that sufficient water be added or generated throughout the reaction to drive the condensation. If water is added at the outset of the reaction it may be added to the reaction mixture as such or be present on the support. This latter approach has been found to be an especially convenient way to introduce the water into the system and it is particularly advantageous from the standpoint of promoting condensation to have all or part of the required water available at the surface of the support. Where the reaction is to be conducted in a continuous or semi-continuous manner, it may be advantageous to continuously meter water into the reaction system or to add it in several increments.

In still another useful embodiment of this process, a portion of the required water is generated in situ, that is, in the reactor during the course of the reaction, by dehydrating the alcohols formed as a result of the condensation. From equation IV it is evident that two molecules of alcohol are obtained from the formation of each —O— linkage thus providing a more than adequate and self-perpetuating source of water to drive the condensation if the alcohol is dehydrated. Considering the case where the transition metal alkoxide is a titanium isopropoxide the overall reactions showing the condensation of two isopropoxide moieties and dehydration of the resulting alcohol would be as follows:

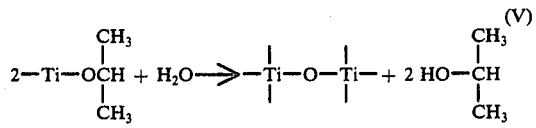

(V)

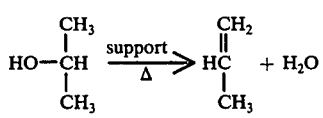

$$\text{HO–CH} \begin{array}{c} CH_3 \\ | \\ | \\ CH_3 \end{array} \xrightarrow[\Delta]{\text{support}} \text{HC} \begin{array}{c} CH_2 \\ \| \\ | \\ CH_3 \end{array} + H_2O \qquad (VI)$$

A small amount of acid, such as sulfuric acid or the like, may be added to the reaction mixture to facilitate the dehydration (equation VI), however, such acid catalysts are not necessary. While it is not essential it is generally advantageous to have a small amount of water such as might be absorbed on a support present at the outset of the reaction to initate condensation and then as the reaction temperature and amount of alcohol in the reactor are increased to generate additional water in situ by dehydration of the alcohol to complete the condensation. It is not necessary that the dehydration product be removed from the reactor, however, when the process is conducted under atmospheric conditions these products will generally be easily removed by venting if the product is a gas (e.g. propene) or by condensing and collecting in a suitable trap where the product is a low boiling liquid.

The weight amount of transition metal bonded to the support matrix will depend on the amount and type of transition metal alkoxide used and the extent of condensation. In general, the transition metal will constitute from about three weight percent of the immobilized catalyst up to about 60% or higher. More generally, between about 5 and 50 weight percent transition metal is bound to the support. To obtain the improved immobilized catalysts, the ratio of transition metal alkoxide molecules to each available hydroxyl group will be greater than 1:1 and up to about $10^6$:1 and, more preferably, between about 1.5:1 and $10^4$:1. With supports having relatively high hydroxyl contents, e.g. $10^{-4}$ to $10^{-3}$ equivalents hydroxyl groups per gram support, this ratio will generally range from about 2:1 to $10^2$:1.

The catalysts of this invention are typically free-flowing powders which are easily handled and because of their hydrolytic stability can be stored for long periods without losing their catalytic activity. They are easily recoverable using conventional filtration procedures and can be reused.

The immobilized catalysts have a complex structure consisting of a highly cross-linked transition metal-containing polymeric network bound to the surface of the support as a result of the reaction of the transition metal alkoxide with the surface hydroxyl groups of the support and polycondensation of the transition metal alkoxide. The polymeric surface coating is a cross-linked matrix of transition metal atoms bonded to each other and the support via bridging oxygen (—O—) linkages. With the improved process of this invention, however, the rigid matrix still contains sufficient unreacted alkoxide groups to have a high degree of catalytic activity. It is believed that these alkoxide groups in addition to being present on the surface of the transition metal oxide polymer may also be present within the matrix. It is possible by this process to completely coat even low hydroxylic content support materials and supports having very irregular surfaces so that only transition metal oxide polymer and alkoxide groups are present on the surface of the immobilized catalyst to a considerable depth.

In general, catalysts of this invention will have utility in any application where transition metal catalysts of Groups IVb, Vb or VIb have previously been employed. Such applications include but are not limited to olefin metathesis and polymerization, cyclooligomerization of alkynes and alkenes, Ziegler-Natta polymerizations, hydrogenation and the like. They are particularly useful with esterification and ester-interchange reactions including transesterifications. The advantages of these immobilized catalysts are many but primarily are their hydrolytic stability, ability to be virtually completely removed at the end of reaction by simple filtration procedures and the fact that virtually all the transition metal is bound to the support and will not be dissolved in the reaction mixture.

The immobilized catalysts have particular utility in the preparation of ester products useful as plasticizers, lubricants, including base-stocks and additives, polymer additives and intermediates and the like. Because the active transition metal catalyst is bound to the surface of the support and not dissolved in the reaction mixture, any color bodies formed which contain the metal are trapped on the surface of the catalyst and can be removed by filtration at the end of the reaction.

Since virtually all the catalyst can be removed from ester products prepared using these supported catalysts, the resulting essentially metal-free esters and polyesters have increased hydrolytic, oxidative and thermal stability. This is a particularly important consideration with ester products which must meet certain requirements with regard to metal content, such as three centistoke (210° F) and one centistoke (500° F) ester turbine lubes which must conform with the rigid specifications of MIL-L-7808 G and MIL-L-27502.

The following examples illustrate the invention more fully. In these examples all parts and percentages are given on a weight basis unless otherwise indicated. Also, unless otherwise specified the support was not dried prior to use and no precautions were taken to exclude moisture from the system.

EXAMPLE I

A supported titanium catalyst was prepared in a jacketed stainless steel reactor equipped with an agitator, thermocouple and condenser with a receiver. The reactor was charged with 90 parts mineral oil (White Oil No. 70) and 10 parts of a naturally acidic montmorillonite clay containing about 4% adsorbed water. Heating and agitation were commenced and subsurface addition of a solution of 33.5 parts tetraisopropyl titanate (Tyzor TPT manufactured by E. I. du Pont de Nemours and Company) in 27.5 parts mineral oil begun. The addition was continued for 1¼ hours during which time the reaction temperature was increased to 110° C. When the temperature reached 120° C a second addition of a solution of 21 parts mineral oil and 34 parts tetraisopropyl titanate was begun. When the temperature reached 140° C distillate began to collect. By the time the temperature reached 170° C and the second addition was complete (addition time 1¼ hours), the rate of distillate recovery had increased significantly. Heating was continued and the temperature increased to about 200°-210° C and maintained for an additional five hours while removing distillate and venting propene and any other volatile products which did not condense. Some foaming was noted, however, it did not interfere with the reaction or collection of the distillate. After cooling to about 70° C the supported catalyst was collected on a filter, washed several times with isopropanol until the filtrate was clear and air-dried. There was a 205% increase in weight of the support. Analysis (atomic absorption) showed the product contained 37.8 weight percent titanium. The supported catalyst was a free-flowing grayish powder which was almost fluid in appearance.

EXAMPLE II

A glass reactor was fitted with an agitator, thermometer and condenser/trap arrangement. A vent line at the top of the condenser led to a dry ice trap. The reactor was charged with 20.1 grams of the naturally acidic montmorillonite clay of Example I, 180 grams mineral oil and 50.3 grams tetraisopropyl titanate. The reaction mixture was heated with agitation to about 200° over a 1 hour period while taking off 27 mls of isopropanol. Ten grams propene were also collected in the dry ice trap. After cooling, the reaction mixture was filtered and washed with isopropanol until a colorless filtrate was obtained. Upon air-drying, 44.2 grams of catalyst containing 21.8% by weight titanium was obtained.

EXAMPLE III

Employing a procedure similar to that described in Example II a supported vanadium catalyst was prepared by reacting 10 grams of the naturally acidic montmorillonite clay and 15 grams tributylvanadate in 160 grams mineral oil by heating the reaction mixture with agitation from room temperature to 250° C over a period of 1¼ hours. Distillate began coming off at about 200° C and a total of 6.2 mls butanol was removed. Butene was also condensed in the dry ice trap. After cooling and filtration the product was washed with isopropanol until the filtrate had only a very pale yellow coloration. The final weight of the product after air-drying was 14.8 grams. The supported catalyst contained 16.1% by weight vanadium.

EXAMPLE IV

In much the same manner, an immobilized zirconium catalyst was prepared. The support used for this reaction was a synthetic silica/alumina (13% as $Al_2O_3$). The alumina/silica support (10.8 grams) was charged to a reactor with 120 grams mineral oil (70 SUS) and 10.1 grams tetrabutylzirconate. The mixture was then gradually heated to about 220° C over a period of about 3 hours while removing butanol and venting gases. After filtering, washing and air-drying 13.25 grams of a supported catalyst (7.3 weight percent zirconium) was obtained.

EXAMPLE V

To demonstrete the versatility of the present invention and the ability to obtain useful immobilized catalysts from a variety of supports, a series of hydroxylic support materials were reacted with tetraisopropyl titanate (TPT) in a 70 SUS mineral oil. The method of reaction was similar to that already described with slight variations in the reaction temperature and reaction time. Details for runs are set forth in Table I. The table sets forth the support used, the charge of the reactants and mineral oil, the maximum reaction temperature, the reaction time, the percent weight increase of the support $$(\frac{Final\ wt.\ -\ Initial\ wt.}{Initial\ wt.} \times 100)$$

and the weight percent titanium bound to the support. From the data provided it is evident that a wide variety of support matrices can be employed to prepare the immobilized catalysts of this invention. It can also be seen that by this process it is possible to obtain catalysts having very high transition metal contents.

EXAMPLE VI 10.25 Grams of the naturally acidic montmorillonite clay, 68.5 grams tetraisopropyl titanate and 170 grams mineral oil (50 SUS) were charged to a reactor and heated to approximately 220° C in 1 1/2 hours during which time 32.5 mls isopropanol and 12 grams propene were removed. The resulting immobilized catalyst contained 35 wt. % titanium. Similar results are obtained when the reaction is conducted in 100 SUS mineral seal oil. With the more viscous oil, however, more foaming is observed and filtering time is somewhat longer.

EXAMPLE VII

A series of reactions were conducted to demonstrate the use of different titanium alkoxides namely, tetrabutyl titanate (VIIa), tetraoctyl titanate (VIIb) and a partially condensed tetrabutyl titanate (VIIc) prepared by controlled addition of an amount of water calculated to obtain a condensation product of 2-3 mols tetrabutyl titanate as per U.S. 2,689,858. Naturally acidic montmorillonite clay and 70 SUS mineral oil were used for each of the reactions. Reaction details and the percent titanium obtained for the resulting immobilized catalysts are as follows:

|  | VIIa | VIIb | VIIc |
|---|---|---|---|
| Parts Charged (Ti compound/support/oil) | 68/11/153 | 24/27/175 | 73/10.5/160 |
| Max. Reaction Temp. (° C) | 250 | 210 | 235 |
| Reaction Time (Hrs.) | 6 | 2 1/4 | 10 |
| % Wt. Increase of Support | 191 | 39 | 264 |
| Wt. % Ti Bound to Support | 25.7 | 4.9 | 29.6 |

TABLE I

| EX. | SUPPORT | PARTS CHARGED (TPT/SUPPORT/OIL) | REACTION TIME (HRS.) | MAXIMUM TEMPERATURE (° C) | % WT. INCREASE OF SUPPORT | WT. % Ti |
|---|---|---|---|---|---|---|
| Va | Activated carbon[1] | 59/11.9/160 | 4 | 250 | 238 | 21.5 |
| Vb | Potassium montmorillonite[2] | 68/10:1/154 | 7 | 250 | 20 | 9.7 |
| Vc | Southern bentonite[3] | 68/10.7/162 | 3.75 | 200 | 225 | 27.7 |
| Vd | Silica/alumina (13% as $Al_2O_3$)[4] | 68.8/10/165 | 2 | 200 | 214 | 31.4 |
| Ve | HCl-treated montmorillonite[5] | 68.2/10.6/170 | 2.5 | 180 | 236 | 22.5 |
| Vf | Sub-bentonite clay | 170/25/325 | 1.5 | 220 | 209 | 41.0 |
| Vg | $H_2SO_4$-treated montmorillonite[7] | 81.4/10.1/178 | 3.75 | 181 | 299 | 33.7 |
| Vh | Naturally acidic montmorillonite | 81.4/10.4/160 | 3 | 195 | 278 | 33.3 |

TABLE I-continued

| EX. | SUPPORT | PARTS CHARGED (TPT/SUPPORT/OIL) | REACTION TIME (HRS.) | MAXIMUM TEMPERATURE (° C) | % WT. INCREASE OF SUPPORT | WT. % Ti |
|---|---|---|---|---|---|---|
| Vi | Calcium silicate[8] | 50.8/10.3/140 | 4.75 | 250 | 170 | 39.6 |
| Vj | Fumed silica[9] | 30.2/6.0/170 | 4.5 | 240 | 560 | 13.5 |
| Vk | Diatomaceous earth (hydrated)[10] | 35.4/5.1/140 | 4 | 242 | 204 | 36.9 |
| Vl | Sulfonated polystyrene resin[11] | 22.5/10/170 | 5.5 | 140 | 90 | 18.3 |

[1]Darco KB; Atlas Chemical Co.
[2]KOH-treated montmorillonite (excess KOH)
[3]Panther Creek Clay; American Colloid Co.
[4]Davison 135 Grade Silica-Alumina
[5]Tonsil FF Optimum; Sud-Chemie
[6]Clarolite BC; Georgia Kaolin Co.
[7]Filtrol Grade 1; Filtrol Corporation
[8]Microcell C; Johns-Manville
[9]Cabosil (M-5); Cabot Corporation
[10]Diatomaceous earth was mixed with water, filtered andair-dried; the support contained > 50% by weight water
[11]Amberlyst 15 Dry; Rohm and Haas (ground to ≧ 60 mesh)

EXAMPLE VIII

An immobilized zirconium catalyst was obtained by reacting 21.3 grams naturally acidic montmorillonite clay and 84 grams tetrabutylzirconate in 140 grams 70 SUS mineral oil. The reaction was conducted for 8½ hours during which time 40 mls butanol and 13.5 grams butene were recovered. For the final 2 hours of reaction the reaction temperature was maintained at 250°-265° C. The final dried catalyst product (51 grams) contained 13.5 wt. % zirconium.

EXAMPLE IX

To demonstrate the versatility of the present invention the following experiments were conducted. Diatomaceous earth (Dicalite) dried at 90° C for about 2 days was employed as the support. About 10.5 grams of the dry support was combined with 60 grams tetraisopropyltitanate in 160 grams 70 SUS mineral oil and the mixture heated with agitation up to a temperature of 250° C for a period of over 2 hours. No reaction was observed as evidenced by the lack of isopropanol and propene formation. Repeating the experiment using the above charges but additionally adding three drops 95% sulfuric acid at the outset of the reaction resulted in the vigorous evolution of isopropanol and butene at 250° C and the production of an immobilized catalyst containing 39.1 wt. % bound titanium. Again, repeating the experiment but with the addition of 0.5% (based on the reactants charged) water at the outset of the reaction resulted in a vigorous reaction with isopropanol and propene evolution and similarly yielded an immobilized catalyst containing 42.3 weight percent titanium.

EXAMPLE X 10.5 Grams activated granular carbon (Witcarb 517), 23.6 grams tetraisopropyl titanate and 140 grams mineral oil were charged to a reactor and heated to 200° C in a period of 1 hour. No reaction was observed. Upon the addition of three drops concentrated sulfuric acid, isopropanol and propene began coming off at a rapid rate. The final catalyst product (23 grams) contained 19.6 wt. % titanium.

EXAMPLE XI

To demonstrate the utility of the catalysts of this invention a hydrogenation was conducted as follows: A 1-liter stainless steel autoclave was charged in a dry nitrogen atmosphere with 500 mls deoxygenated xylene, 50.5 mls (0.5 mol) cyclohexane, 26.5 mls (0.25 mol) toluene, 32 mols 24.8% diisobutylaluminum hydride (0.04 mol) in heptane and 3.0 grams (0.01 mol Ti) of the immobilized titanium catalyst of Example I. The autoclave was then pressurized to 500 psig with heating and agitation (500 rpm). At 87° C gas was bled to adjust the pressure to 500 psig and heating continued. Initial hydrogen uptake was noted at 180° C (565 psig). When the temperature reached 200° C heating was terminated and the reactor and its contents allowed to slowly cool to 180° C (375 psig) and then to room temperature. Gas — liquid chromatographic analysis showed almost complete conversion of cyclohexene to cyclohexane.

EXAMPLE XII

To further demonstrate the utility of the immobilized catalyst of this invention a hydroxyl-terminated polyester product useful in the preparation of urethane polymers was prepared by reacting 364 parts 1,4-butanediol and 1076 parts 1010 Dimer Acid containing 97% $C_{36}$ dibasic acid and 3% $C_{54}$ tribasic acid. The reaction mixture was heated with 0.05 parts 50% $H_3PO_2$ solution to 225° C while removing water. A moderate vacuum was pulled on the system to facilitate water removal. When the acid value reached about two, 1 gram of the catalyst of Example I was added to the reaction mixture and the vacuum was increased while maintaining the temperature. The polymerization was continued for an additional 20 minutes until distillate collection was completed. The resulting polyester product had excellent clarity and color, contained less than 3 ppm titanium and readily reacted with diisocyantes to obtain useful polyurethane products.

EXAMPLE XIII

A mixed ester product useful as an industrial lubricant for metal working applications, e.g. as a rolling oil, and which is readily emulsifiable in water was prepared using the immobilized titanium catalyst of Example I. 288 Grams (1.0 equivalent) refined palm oil, 60 grams (0.3 equivalent) polyoxyethylene glycol having an average molecular weight of 400 and 85.8 grams (0.3 equivalent) Empol 1014 Dimer Acid containing 95% $C_{36}$ dibasic acid were charged to a reactor with 0.01 wt. % (based on the total reactant charge) of the immobilized titanium catalyst and the reaction mixture heated to 220° C for about 5 hours while removing water. After cooling, the reaction product was filtered using a 0.5% diatomaceous earth filtering aid. The final product had an acid value less than 20, was readily emulsifiable in cold tap water with moderate agitation and the resulting aqueous emulsion also had good stability. The modified triglyceride had good thermal stability and lubrication properties and contained less than 1 ppm titanium.

EXAMPLE XIV

|  | XVa | XVb | XVc |
|---|---|---|---|
| Parts Charged (Ti compound/support/oil) | 20.3/40.4/150 | 45.6/30.5/160 | 67.5/10/138.5 |
| TPT/Support | 0.50 | 1.5 | 6.75 |
| Max. Reaction Temp. (° C) | 185 | 200 | 210 |
| Reaction Time (Hrs.) | 1 | 1 | 1 |
| % Wt. Increase of Support | 32 | 57 | 205 |
| Wt. % Ti Bound to Support | 7.9 | 20.3 | 37.8 |

The following experiment was conducted to provide comparative data and further point out the advantages of the catalysts of this invention. A polymeric orthotitanic acid ester catalyst similar to the heterogeneous catalysts of German Pat. No. 1,142,868 was prepared from ethylene glycol and tetrabutyl titanate. To prepare the catalyst, 62 grams polymer grade ethylene glycol (dried prior to use) and 83.6 grams tetrabutyl titanate were reacted by heating at about 130°–150° C. Within a very short time a white suspension formed and 30 mls butanol were collected. After cooling the reaction mixture was filtered and the catalyst washed with hot xylene and dried in a vacuum oven at 110° C. The heterogeneous polymeric catalyst contained 35.5 wt. % titanium.

To evaluate the catalyst, a mixed ester product obtained by esterifying azelaic acid, phthalic anhydride and mixed saturated aliphatic mono- and dibasic acids (75:25) with excess propylene glycol (0.625:0.222:0.150:1.25 equivalents ratio of the respective reactants) was obtained by heating the reactants up to 230° C for about 9 hours in the absence of catalyst while removing water. The resulting mixed ester product had an acid value of 5.4 and 100° F kinematic viscosity of 430 centistokes. The color (percent transmittance (%T) determined at 440 and 550 millimicrons by spectrophotometric analysis) was 35/82.

To 1000 grams of this mixed ester product was added 0.031 wt. % of the above-prepared heterogeneous catalyst (110 ppm Ti). The reaction mixture was then heated at 225° C under high vacuum (1-2 mm Hg) for 2 hours while removing glycol from the reaction mixture. After 2 hours, the acid value was decreased to 0.4 with a corresponding increase in viscosity. The color of the product darkened so that the percent transmittance was a very unsatisfactory 4/48. In addition to the poor color, the polyester product (after filtration to remove the heterogeneous catalyst) contained 86 ppm titanium.

The above operation was repeated using 1000 grams of the mixed ester and heating for 2 hours at 225° C and 1-2 mm Hg. In this reaction, however, 0.057 wt. % of an immobilized titanium catalyst (186 ppm Ti) similar to that of Example Vg was used. The resulting polyester had an increased viscosity, acid value of 0.5 and much improved color (% T=19/75). Even though a much higher level of titanium was present in the reaction mixture, the final polyester product contained only 2.4 ppm Ti after filtering to remove the immobilized catalyst.

EXAMPLE XV

To further demonstrate the superiority of the immobilized catalysts of this invention, the following catalysts were prepared using tetraisopropyl titanate, the naturally acidic montmorillonite support and 70 SUS mineral oil in accordance with the usual procedure. Reaction details and product analyses were as follows:

For comparison with the above-prepared immobilized titanium catalyst, a heterogeneous catalyst (identified as XVd) was prepared from tetraisopropyl titanate and the same naturally acidic montmorillonite clay in accordance with the teachings of Brooks et al U.S. Pat. No. 3,817,931. The reaction was conducted under anhydrous conditions. The clay (9.69 grams) calcined under nitrogen for 2 hours at 350° C to remove water was charged to a reactor with 70.18 grams tetraisopropyl titanate and 160 grams anhydrous toluene. The reaction mixture was heated with agitation at about 25° C for about 19 hours and then filtered. 10.2 Grams catalyst was obtained after washing and air drying. The catalyst contained only 2.9 wt. % bound titanium even though the TPT/Support ratio was identical to that used in the preparation of immobilized catalyst XVc.

For use in evaluating the above catalysts, a mixed ester product was prepared. The mixed ester was obtained by reacting adipic acid, 1,3-butylene glycol and 2-ethylhexanol (equivalents ratio 1.0:1.125:0.125) at a temperature of 225° C while removing water. To facilitate water removal a vacuum was applied during the latter stages of the reaction. When the acid value reached about 25 the reaction was terminated. The resulting ester product has an acid value of 25.4, 100° F viscosity of 197 centistokes and percent transmittance of 98/100. One-thousand grams of this product was used in each of the subsequent catalyst evaluations which were conducted as follows:

1000 Grams of the ester product to which was added 0.01 wt. % catalyst was heated to 225° C in a nitrogen atmosphere. A vacuum (123 mm Hg) was then applied to the system while maintaining the temperature at 225° C. When 9.5 mls water was recovered the vacuum was lowered to 0.8 mm Hg and the reaction continued for exactly 30 minutes. At this point heating was terminated and the vacuum broken with nitrogen. 1.5 Wt. % diatomaceous earth filtering aid was added when the reaction mixture had cooled to 195° C and the mixture filtered. Acid value, kinematic viscosity and color were then obtained for each polyester product. The results are as follows:

| POLYESTER PREPARED USING CATALYST: | XVa | XVb | XVc | XVd |
|---|---|---|---|---|
| Acid Value | 1.1 | 0.8 | 0.6 | 1.4 |
| 100° F Viscosity (cs) | 994 | 1440 | 1740 | 876 |
| Color (% T at 440/550 mμ) | 95/97 | 93/97 | 92/96 | 93/98 |

It is evident from the greater kinematic viscosities obtained with products XVa, XVb and XVc that more efficient and more active catalysts are provided by this invention.

The catalyst was analyzed by Auger electron spectroscopy by pressing the powdered catalyst onto a stainless steel mesh mounted at approximately a 30° angle to the electron beam. Standard Auger derivative spectra were obtained using a beam energy greater than 6500 electron volts and a beam current of 1-4 milliamps to analyze the $L_3M_{2,3}M_{2,3}$ Auger electron for Ti (387 e.v.) and the $KL_2L_2$ Auger electron for Si (1619 e.v.). Each titanium and silicon peak was scanned at least ten times, the average value for the peak to peak distance was determined and the ratio of peak heights calculated. The Ti/Si peak height ratio obtained for catalyst XVd was 0.13 whereas for catalysts XVa and XVb the values were 1.3 and 10.5, respectively. With catalyst XVc, any silicon that might be present on the surface, i.e. the first few monolayers of the support was below the detection limits of the instrument. While the results obtained are not quantitive, they do nevertheless qualitatively demonstrate that an increased amount of titanium is available at the surface of the immobilized catalysts of this invention. The data also indicates that it is possible to essentially completely coat an acidic clay support following the process of this invention.

To demonstrate the improved hydrolytic stability of the immoblized catalysts of this invention, catalysts XVc and XVd were treated with aqueous isopropanol. 54 Grams of each catalyst was combined with 76 grams isopropyl alcohol (91%) and 135 grams water and the mixture refluxed at 84° C for 2 hours. The mixture was then filtered, and the catalyst washed with isopropanol and the resulting catalysts respectively identified XVch and XVdh. After the above treatment catalyst XVch contained 38.2 wt. % bound titanium and catalyst XVdh contained 2.8 wt. % bound titanium. Both catalysts (0.01 wt. %) were evaluated for activity with the mixed ester prepared above in accordance with the previously described procedure. The following results were obtained:

| POLYESTER PREPARED USING CATALYST: | XVch | XVdh |
|---|---|---|
| Acid Value | 0.8 | 1.3 |
| 100° C Viscosity (cs) | 1540 | 822 |

It is readily apparent that catalyst XVc retains most of its activity after such water treatment and catalyst XVdh had approximately the same activity as the untreated naturally acidic clay support which upon evaluation (using the same procedure) yielded a polyester having an acid value of 1.7 and 100° F viscosity of 802 centistokes.

EXAMPLE XVI

A one-liter autoclave was charged with 20 grams of the naturally acidic montmorillonite clay of Example I, 361 grams 70 SUS mineral oil and 137 grams tetraisopropyl titanate. The reaction mixture was stirred (400 rpm) and heating commenced. The temperature was maintained at 200° C for 4½ hours during which time the pressure increased from 140 psig and finally stabilized at 450 psig. The reactor and its contents were cooled to room temperature (30 psig) and slowly vented to two contiguous dry ice traps. 18.25 Grams propene was recovered. The catalyst, after washing and drying, weighed 54.9 grams and contained 40.7 wt. % titanium.

We claim:

1. In a process for preparing a supported transition metal catalyst by the reaction of a hydroxylic support with a transition metal alkoxide of the formula $$M(OR)_nQ_m$$

where M is a transition metal selected from Groups IVb, Vb and VIB, OR is an alkoxy radical containing 1 to 18 carbon atoms, n is an integer from 2 up to the valence of the metal M, Q is an inert group which will not react with the hydroxyl groups of the support, the alkoxide radical OR or alcohol ROH formed therefrom and m is an integer so that n + m statisfies the valence of the metal M, to obtain a free-flowing, hydrolytically stable catalyst having superior activity and having the transition metal bound to the surface thereof, the improvement consisting essentially of: heating the support and an excess of transition metal alkoxide, based on the available surface hydroxyl groups, in an inert hydrocarbon in the presence of water at a temperature in the range 100°-300° C to effect condensation of the transition metal alkoxide and reaction of the transition metal alkoxide or oligomer thereof with the surface hydroxyl groups.

2. The process of claim 1 wherein the transition metal alkoxide is selected from the group of compounds wherein the transition metal M is titanium, zirconium, halfnium or vanadium and all the valences of the transition metal are filled with a saturated branched- or straight-chain alkoxy radical containing 2 to 8 carbon atoms or a radical =O is bonded to the transition metal with the remaining available valences of the transition being filled with saturated branched- or straight-chain alkoxy radicals having 2 to 8 carbon atoms.

3. The process of claim 2 wherein the ratio of transition metal alkoxide molecules per surface hyroxyl group is greater than 1:1 and up to $10^6:1$, the inert hydrocarbon is an aliphatic hydrocarbon and the weight ratio of hydrocarbon to support is between about 0.5:1 and 50:1.

4. The process of claim 3 wherein all or a portion of the water is absorbed on the surface of the hydroxylic support.

5. The process of claim 4 wherein the hydroxylic support is selected from the group consisting of silica, alumina and mixtures thereof.

6. The process of claim 3 wherein all or a portion of the water is generated in situ by dehydration of alcohols.

7. The process of claim 6 wherein the transition metal alkoxide is tetraisopropyl titanate.

8. The process of claim 3 wherein M is a metal selected from the group consisting of titanium, zirconium, hafnium or vanadium and OR is a saturated branched or straight-chain alkoxy radical containing 2 to 8 carbon atoms.

9. The process of claim 8 wherein the transition metal alkoxide is a titanium tetraalkoxide.

10. The process of claim 8 conducted at a temperature in the range 120°-250° C in an aliphatic essentially saturated liquid hydrocarbon having a boiling point greater than about 140° C and the ratio of transition metal alkoxide molecules per hydroxyl group available on the support is between about 1.5:1 and $10^4:1$.

11. The process of claim 10 wherein the hydroxylic support is selected from the group consisting of silica, alumina or mixtures thereof and the weight ratio of the hydrocarbon to support is between about 2:1 and 25:1.

12. The process of claim 11 wherein the hydrocarbon solvent is a mineral oil, the transition metal alkoxide is a titanium tetraalkoxide and the ratio of the transition tetraalkoxide molecules per available hydroxyl group is between about 2:1 and $10^2$:1.

13. A supported transition metal catalyst obtained by the process of claim 1 and containing from about 3 to 60 weight percent bound transition metal.

14. The supported metal catalyst of claim 13 wherein the transition metal is selected from the group consisting of titanium, zirconium, hafnium or vanadium.

15. The supported transition metal catalyst of claim 14 wherein OR is a saturated branched or straight-chain alkoxy radical containing 2 to 8 carbon atoms and the reaction is conducted at a temperature in the range 120°–250° C in an aliphatic essentially saturated liquid hydrocarbon with a ratio of transition metal alkoxide molecules per hydroxyl group of 1.5:1 to $10^4$:1 and weight ratio of hydrocarbon to support between 0.5:1 and 50:1.

16. The supported transition metal catalyst of claim 15 wherein the hydrocarbon has a boiling point higher than 140° C, the support is selected from the group consisting of silica, alumina or mixtures thereof and the weight ratio of the hydrocarbon to support is between about 2:1 and 25:1.

17. The supported transition metal catalyst of claim 14 wherein about 5 to 50 weight percent titanium is bound to the support.

18. The supported transition metal catalyst of claim 17 obtained by the reaction of a titanium tetraalkoxide wherein the alkoxide group is a saturated branched or straight-chain radical containing 2 to 8 carbon atoms and the ratio of titanium alkoxide molecules per hydroxyl group of the support is between about 1.5:1 and $10^4$:1.

19. The supported transition metal catalyst of claim 18 wherein the hydrocarbon is an aliphatic essentially saturated liquid hydrocarbon having a boiling point greater than about 140° C and the weight ratio of hydrocarbon to support is between 2:1 and 25:1.

20. The supported transition metal catalyst of claim 19 wherein the support is selected from the group consisting of silica, alumina or mixtures thereof.

21. The supported transition metal catalyst of claim 20 wherein the hydrocarbon is mineral oil, the titanium tetraalkoxide is tetraisopropyl titanate or tetrabutyl titanate and the ratio of titanium tetraalkoxide molecules per hydroxyl group is between about 2:1 and $10^2$:1.

22. The supported transition metal catalyst of claim 21 wherein th support is an acidic montmorillonite clay.

23. An immobilized transition metal catalyst characterized as being hydrolytically stable, finely divided and a free — flowing powder containing from about 3 to 60 weight percent of transition metal selected from groups IVb, Vb and VIb, said transition metal being present on and bound to the support matrix by bridging oxygen linkages as a polymeric cross-linked network wherein the transition metal atoms are bonded to each other by bridging oxygen linkages.

24. The immobilized transition metal catalyst of claim 22 wherein the support matrix is essentially completely coated with the polymeric cross-linked network wherein the transition metal atoms are bonded to each other by bridging oxygen linkages.

25. The immoblized transition metal catalyst of claim 23 wherein the support is selected from the group consisting of silica, alumina or mixtures thereof.

26. The immobilized catalyst of claim 23 wherein the transition metal is selected from the group consisting of titanium, zirconium, hafnium and vanadium.

27. The immobilized catalyst of claim 26 containing from about 5 to 50 weight percent bound transition metal.

28. The immobilized catalyst of claim 27 wherein the transition metal is titanium.

* * * * *